US010010402B2

(12) United States Patent
Wang et al.

(10) Patent No.: US 10,010,402 B2
(45) Date of Patent: Jul. 3, 2018

(54) THORACIC AORTIC COVERED STENT

(71) Applicant: LIFETECH SCIENTIFIC (SHENZHEN) CO., LTD, Guangdong (CN)

(72) Inventors: Yongsheng Wang, Guangdong (CN); Caiping Liu, Guangdong (CN); Deyuan Zhang, Guangdong (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 10 days.

(21) Appl. No.: 15/039,142

(22) PCT Filed: Nov. 7, 2014

(86) PCT No.: PCT/CN2014/090604
§ 371 (c)(1),
(2) Date: May 25, 2016

(87) PCT Pub. No.: WO2015/078289
PCT Pub. Date: Jun. 4, 2015

(65) Prior Publication Data
US 2017/0156846 A1    Jun. 8, 2017

(30) Foreign Application Priority Data
Nov. 28, 2013    (CN) .......................... 2013 1 0627534

(51) Int. Cl.
*A61F 2/915*    (2013.01)
*A61F 2/07*    (2013.01)
(Continued)

(52) U.S. Cl.
CPC .................. *A61F 2/07* (2013.01); *A61F 2/89* (2013.01); *A61F 2/915* (2013.01);
(Continued)

(58) Field of Classification Search
CPC ...... A61F 2/07; A61F 2/915; A61F 2002/825; A61F 2002/91583
See application file for complete search history.

(56) References Cited

U.S. PATENT DOCUMENTS

| 6,585,757 B1 * | 7/2003 | Callol ....................... A61F 2/90 |
| | | 623/1.16 |
| 2006/0195177 A1 * | 8/2006 | Kaufmann ................ A61F 2/07 |
| | | 623/1.16 |

(Continued)

FOREIGN PATENT DOCUMENTS

| CN | 2817768 Y | 9/2006 |
| CN | 202554170 U | 11/2012 |
| CN | 203576697 U | 5/2014 |

OTHER PUBLICATIONS

Office Action dated Apr. 3, 2015 in China priority application No. CN201310627534.2.
(Continued)

*Primary Examiner* — Christopher D Prone
*Assistant Examiner* — Suba Ganesan
(74) *Attorney, Agent, or Firm* — Raymond Sun

(57) ABSTRACT

The present invention relates to a thoracic aortic covered stent (100), comprising a bare stent segment (110) and a covered stent segment (120). The bare stent segment (110) comprises a bare wave-shaped ring (111); the covered stent segment (120) has a lesser curvature side region (100*c*), a greater curvature side region (100*a*), and two opposite intermediate regions (100*b*) located between the lesser curvature side region (100*c*) and the greater curvature side region (100*a*) respectively; and the covered stent segment (120) comprises a first proximal wave-shaped ring (121). The stent (100) further comprises a first connecting member (131), a first side connecting member (132) and a second side connecting member (133) all connected to the bare
(Continued)

wave-shaped ring (111) and the first proximal wave-shaped ring (121), wherein the first connecting member (131) is arranged in the lesser curvature side region (100c), and the first side connecting member (132) and the second side connecting member (133) are arranged in the two intermediate regions (100b) respectively. The stent (100) when located near the lesser curvature side (22) with a relatively small radius of curvature has a connecting assembly rigidly connecting the bare stent segment (110) and the covered stent segment (120), and through the constraints thereof, the bare stent segment (110) can be effectively prevented from overturning towards the vessel wall during the release process, so that the proximal end of the covered stent segment (120) is securely apposed to the wall, thereby avoiding the "turnover" effect.

10 Claims, 8 Drawing Sheets

(51) Int. Cl.
*A61F 2/89* (2013.01)
*A61F 2/82* (2013.01)

(52) U.S. Cl.
CPC ... *A61F 2002/075* (2013.01); *A61F 2002/825* (2013.01); *A61F 2002/91508* (2013.01); *A61F 2220/0058* (2013.01); *A61F 2220/0075* (2013.01); *A61F 2230/0067* (2013.01); *A61F 2250/0039* (2013.01)

(56) References Cited

U.S. PATENT DOCUMENTS

| 2008/0195191 A1* | 8/2008 | Luo | A61F 2/07 623/1.13 |
| 2011/0166644 A1* | 7/2011 | Keeble | A61F 2/07 623/1.24 |

OTHER PUBLICATIONS

Office Action dated Aug. 13, 2015 in China priority application No. CN201310627534.2.

\* cited by examiner

THORACIC AORTIC COVERED STENT

TECHNICAL FIELD

The present invention relates to the technical field of medical devices, in particular to a thoracic aortic covered stent.

BACKGROUND OF THE PRESENT INVENTION

Aortic diseases mainly include aortic dissection and aortic aneurysm; the aortic aneurysm is further divided into true aortic aneurysm and false aortic aneurysm. The aortic aneurysm or aortic dissection, with mortality rate higher than 50% within 48 hours and higher than 85% within two weeks after the onset, is a very dangerous disease which has been a serious threat to human health. With the advent of China's aging population trends, the incidence thereof will be constantly rising.

Taking the thoracic aortic dissection as an example, as shown in FIG. 1, an aorta 1 includes an ascending aorta 11 connected to the heart, a descending aorta 12, and an aortic arch 13 between the two; the descending aorta 12 comprises a thoracic aorta 21 and an abdominal aorta (not shown in the figure); the aortic arch 13 has three branch vessels comprising an innominate artery 15, a left common carotid artery 16 and a left subclavian artery 17. Due to the damage of the aortic intima, the high pressure blood flows through a dissection crevasse 18 and rushes into the vessel wall to tear the tunica media, so that the integrated structure of the aortic wall is divided into two parts, and a dissection lumen 20 is formed in a chapped gap between the inner and outer walls of the dissection. In order to distinguish it from the aortic lumen, the dissection lumen 20 is called as a false lumen, whereas the aortic lumen is called a true lumen. The dissection lumen 20 is located at a greater curvature side 19 of the thoracic aorta 21, and may also be formed at a lesser curvature side 22 of the thoracic aorta.

At present, surgical treatments on these diseases mainly refer to traditional open heart surgery and minimally invasive endovascular exclusion surgery. The surgical treatments present great difficulty, are difficult operations, involve long operation time, often result in heavy wounds to patients, and have high mortality rates. Meanwhile, assistive technologies, such as deep hypothermic circulatory arrest, cerebral perfusion, conventional cardiopulmonary bypass, rising and decreasing temperature, cardiovascular anesthesia and etc., are also required. In addition, pipelines in the surgical field are numerous and have complex order and many anastomotic stomas, resulting in prolonging the operation time and correspondingly prolonging the cerebral ischemia time and extracorporeal circulation time, thereby increasing the operative mortality rates and complications (especially cerebral complications).

In the minimally invasive interventional treatment technology using the lumen isolation principle, the covered stent is usually used for isolating the blood flow from the aortic aneurysm or aortic dissection. Aortic covered stents on the current market mainly consist of a metal wire and PET (Polyethylene Terephthalate Resin) membrane or ePTFE (Polytetrafluoroethylene) membrane covered on the metal wire, the metal wire is made into a straight tube-shaped stent frame and covered by the PET membrane or ePTFE membrane. A covered stent in a compressed state is conveyed into the human body through a delivery system with a relatively small luminal diameter under the guidance of a guide wire positioned in advance, accurately released after reaching the position of a diseased vessel with the help of a developing system, and covered on the diseased vessel segment to isolate the lesion and to form a new blood flow channel. For the aortic aneurysm, after losing the blood supply, the blood remained in the tumor cavity is gradually formed into thrombus and muscularized to form vascular tissues, the aneurismal wall in an extended state is constricted due to a negative pressure, and gradually restored to solve the primitive form, thereby achieving the purpose of treating the aortic aneurysm. For the aortic dissection, the aortic dissection crevasse is covered by the covered stent, the thrombus is gradually formed in the false lumen, and the negative pressure is gradually decreased, thereby achieving the purpose of treating the aortic dissection.

At present, the thoracic aortic covered stent (hereinafter referred to as stent) includes two kinds such as one with a bare stent segment at a proximal end and the other without a bare stent segment at the proximal end, wherein the bare stent segment here refers to a metal wire tube-shaped part not covered by a membrane. In the industry, the proximal end and the distal end of the stent are defined according to the blood flow direction, and the blood flows to the distal end from the proximal end of the stent. The bare stent segment at the proximal end may lengthen an anchoring region at the proximal end of the stent without blocking the branch vessels on the aortic arch, and will improve the apposition performance of the covered proximal end of the stent to the wall. Therefore, the stent has better adaptability for patients with a dissection crevasse in the thoracic aorta relatively close to the branch vessels on the aortic arch, or with relatively short thoracic aortic aneurysm neck.

In the existing stent, the bare stent segment is usually fixed to the proximal end of the membrane by suturing, so the bare stent segment and the covered stent segment are in flexible connection, in order to ensure the overall flexibility after the stent is implanted. However, during the endovascular release process of the stent, the stent is pushed by a deployer at the distal end of the stent, and gradually released from the proximal end to the distal end; due to the flexible connection between the bare stent segment and the covered stent segment, the pushing force will probably cause the metal wire in the bare stent segment to overturn towards the vessel wall and to contact with the vessel wall, so that the proximal end of the covered stent segment may not be securely apposed to the wall, thereby resulting in the "turn-over effect". Once there is a "turnover" effect", not only the metal wire overturned in the bare stent segment will damage the blood vessel, but also I type endoleak is easily generated between the stent and the blood vessel, namely due to the proximal end of the stent and the blood vessel being not completely enclosed, the blood continuously flows into the aortic aneurysm or the aortic dissection, thereby resulting in continually growing of the aneurysm cavity or the dissection cavity, and leading to the treatment failure and ultimately leading to serious consequences such as rupture.

SUMMARY OF THE PRESENT INVENTION

An object of the present invention is to provide a thoracic aortic covered stent which prevents a metal wire in a bare stent segment from overturning towards the vessel wall.

A technical solution provided by an embodiment of the present invention is that a thoracic aortic covered stent is provided, including a bare stent segment and a covered stent segment, the bare stent segment including a bare wave-shaped ring; the covered stent segment having a lesser curvature side region, a greater curvature side region, and two opposite intermediate regions located between the lesser curvature side region and the greater curvature side region; and the covered stent segment including a first proximal wave-shaped ring, wherein the stent further includes a first connecting member, a first side connecting member and a second side connecting member all connected to the bare wave-shaped ring and the first e proximal wave-shaped ring; the first connecting member is located in the lesser curvature side region, and the first side connecting member and the second side connecting member are located in the two intermediate regions.

In the thoracic aortic covered stent according to the embodiment of the present invention, the bare wave-shaped ring and the first proximal wave-shaped ring both include wave peaks, wave troughs and supports connected and arranged between the wave peaks and the wave troughs, and wherein the two ends of the first connecting member, the first side connecting member and the second side connecting member are both connected to the supports.

In the thoracic aortic covered stent according to the embodiment of the present invention, the first connecting member, the first side connecting member and the second side connecting member are all connected to the supports through steel jackets.

In the thoracic aortic covered stent according to the embodiment of the present invention, the covered stent segment further includes a plurality of wave-shaped rings, a second distal wave-shaped ring and a first distal wave-shaped ring arranged from the proximal end to the distal end; the stent further includes a main body connecting assembly in the greater curvature side region for rigidly connecting the first proximal wave-shaped ring, the plurality of wave-shaped rings and the second distal wave-shaped ring in sequence.

In the thoracic aortic covered stent according to the embodiment of the present invention, the main body connecting assembly is linear.

In the thoracic aortic covered stent according to the embodiment of the present invention, the main body connecting assembly includes a plurality of connecting members, in which each connecting member is rigidly connected with the adjacent wave-shaped rings.

In the thoracic aortic covered stent according to the embodiment of the present invention, the stent further includes a distal connecting assembly in the intermediate regions for rigidly connecting the first distal wave-shaped ring and the second distal wave-shaped ring.

In the thoracic aortic covered stent according to the embodiment of the present invention, there are two distal connecting assemblies symmetrically arranged with respect to the lesser curvature side region.

In the thoracic aortic covered stent according to the embodiment of the present invention, along the direction from the lesser curvature side region to the large lesser curvature side region, the wave height of the bare wave-shaped ring is gradually decreased, and the waveform fillet is gradually increased.

In the thoracic aortic covered stent according to the embodiment of the present invention, the covered stent further includes a wave-shape ring located between the bare wave-shaped ring and the first proximal wave-shaped ring, wherein the bare wave-shaped ring and the other wave-shaped rings are connected by suturing.

The thoracic aortic covered stent provided by the present invention, at near the lesser curvature side with a relatively small radius of curvature, has a connecting assembly rigidly connecting the bare stent segment and the covered stent segment, and through the constraints thereof, the bare stent segment can be effectively prevented from overturning towards the vessel wall during the release process, so that the proximal end of the covered stent segment is securely apposed to the wall, thereby avoiding the "turnover" effect.

BRIEF DESCRIPTION OF THE DRAWINGS

The present invention will be further illustrated as below with reference to accompanying drawings and embodiments, in the drawings.

DETAILED DESCRIPTION OF THE PRESENT INVENTION

In order to understand the technical characteristics, the objects and the effects of the present invention more clearly, the specific implementation ways of the present invention will be described in detail with reference to the accompanying drawings.

Figure 1:
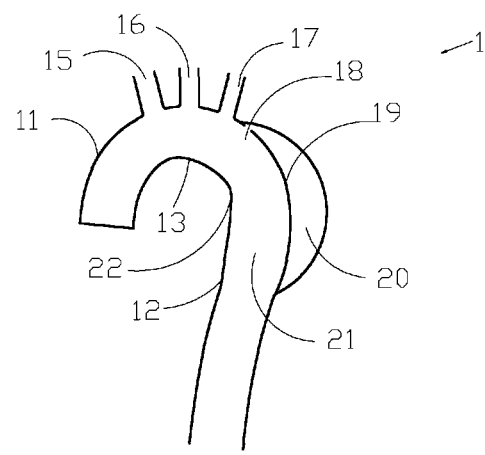
FIG. 1 is a schematic diagram of a thoracic aortic dissection.
Figure 2:
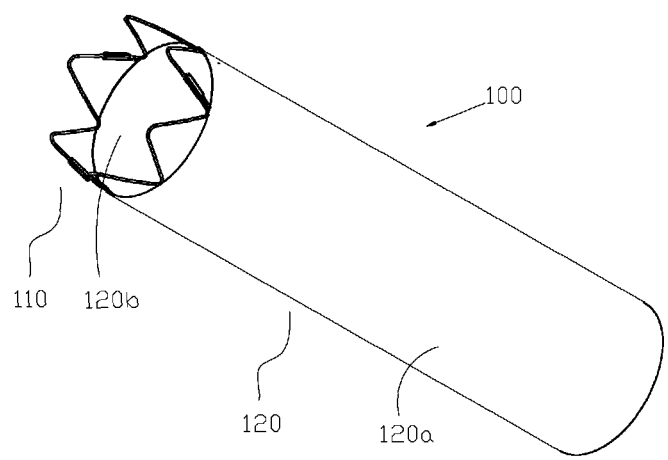
FIG. 2 is a schematic diagram of a thoracic aortic covered stent according to an embodiment of the present invention.
Figure 3:
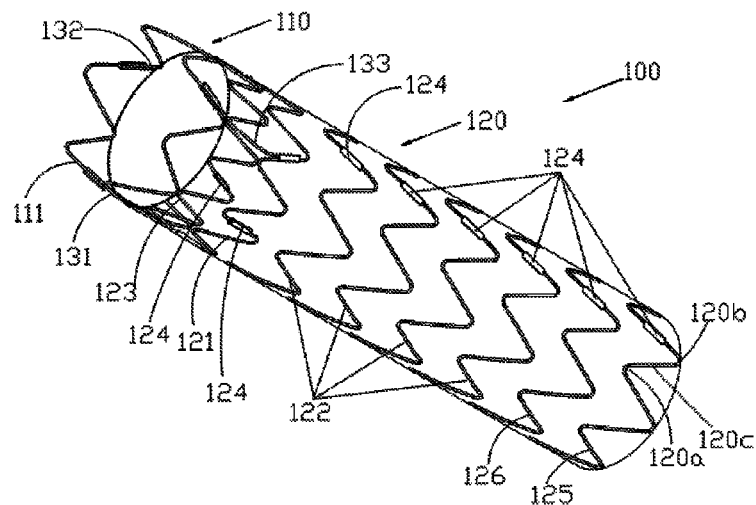
FIG. 3 is a perspective drawing of the stent in FIG. 2.

With reference to FIG. 2 and FIG. 3 a thoracic aortic covered stent 100 (hereinafter referred to as stent) of an embodiment of the present invention includes a bare stent segment 110 and a covered stent segment 120 along an axial direction from the proximal end to the distal end sequentially, and a connecting assembly for rigidly connecting the bare stent segment 110 and the covered stent segment 120.

The covered stent segment 120 includes a plurality of wave-shaped rings 121, 122, 123, 125 and 126, and a membrane 120a; the membrane 120a is fixed on the plurality of wave-shaped rings to connect the plurality of wave-shaped rings so as to enclose and form a lumen 120b with a vertical axis; when the stent is implanted into the blood vessel, the lumen 120b acts as a channel for the blood to flow through.

The plurality of wave-shaped rings are spaced-apart in sequence from the proximal end to the distal end, preferably spaced-apart and arranged in parallel, and include a first proximal wave-shaped ring 121, a plurality of body wave-shaped rings 122, a first distal wave-shaped ring 125 and a second distal wave-shaped ring 126 successively. The wave-shaped rings all include a plurality of proximal vertices 120a, a plurality of distal vertices 120b, and supports 120c connecting the adjacent proximal vertex 120a and distal vertex 120b, the proximal vertices 120a and the distal vertices 120b corresponding to wave peaks and wave troughs, respectively. The plurality of wave-shaped rings has the same or similar waveform, for example, the wave-shaped rings may be Z-shaped wave, V-shaped wave or sine wave and so on.

Not only the waveform of the wave-shaped ring may be set as required, but also the number and the height of the waveforms in each circle wave-shaped ring may be set as required. For example, the first proximal wave-shaped ring may be set to have 8 waveforms with a wave height of 12 mm which are uniformly shaped, according to the position of the stent 100 to be implanted in the thoracic aorta. One of the body wave-shaped rings 122 may have 7 waveforms with a wave height of 12 mm which are uniformly shaped, and the number of the body wave-shaped rings is not more than 5. Each of the first distal wave-shaped ring 125 and the second distal wave-shaped ring 126 may have 7 waveforms with a wave height of 14 mm which are uniformly shaped.

The thoracic aortic covered stent 100 may be prepared in the following manner: a required waveform is formed by braiding a metal wire or by cutting, the metal wire may be a nickel-titanium wire with a wire diameter such as 0.55 mm; after heat setting, two ends of the metal wire are both inserted into a first steel jacket 124, and fixed together by a way of mechanical compaction, so the metal wire and the first steel jacket 124 are fastened together to form a wave-shaped ring. After the manufacturing of the wave-shaped ring is finished, the surfaces of the plurality of wave-shaped rings that are spaced-apart in sequence are covered by a membrane. For example, an inner surface and an outer surface of the plurality of wave-shaped rings may be both covered by e-PTFE membrane integrally, the plurality of wave-shaped rings are located between the two membranes, and the e-PTFE membranes on the inner and outer surfaces are bonded together by a way of high temperature pressing, thereby the plurality of wave-shaped rings are fixed together between the membranes.

Of course, when the wave-shaped ring is formed by integrally cutting a metal tube, the first steel jacket 124 is not required to fix the two ends of the same braiding wire. Or, the two endpoints of the same metal wire may be fixed together by welding so as to form a wave-shaped ring.

The bare stent segment 110 includes at least one bare wave-shaped ring 111 which is uncovered, and the bare wave-shaped ring 111 may be prepared by a method similar to that of the wave-shaped ring in the covered stent segment 120, not described here in detail. Even though FIG. 2 and FIG. 3 show the provision of one wave-shaped ring 111, but it should be known that the structure is only used for illustration, but does not limit the present invention.

Figure 4:
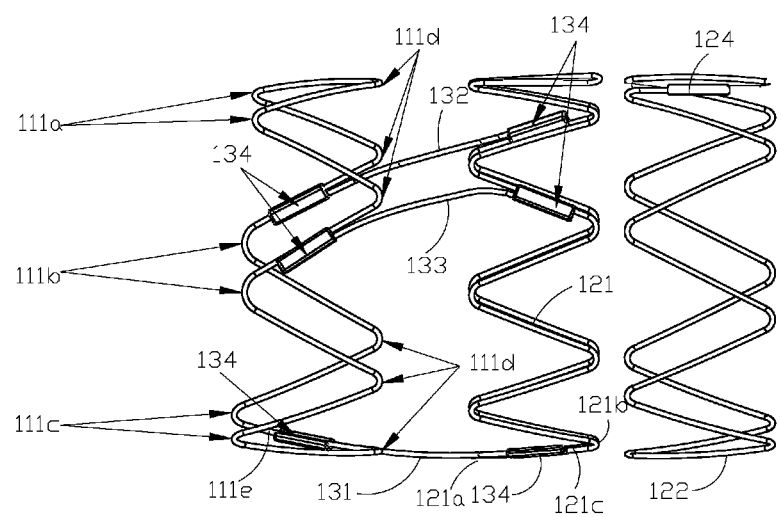
FIG. 4 is a local schematic diagram of the stent in FIG. 3.
Figure 5:
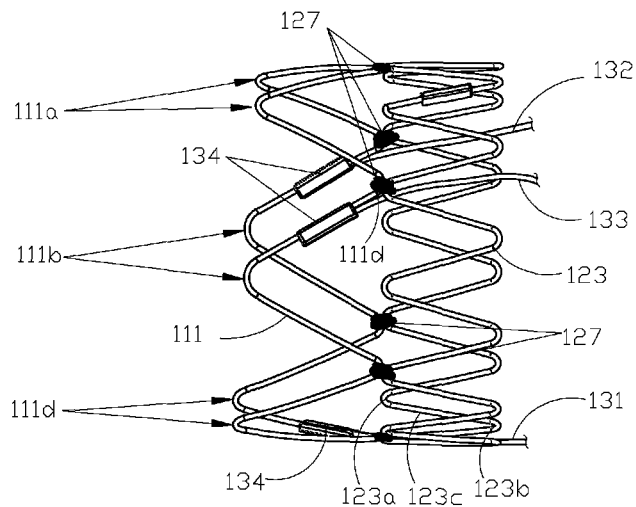
FIG. 5 is a local schematic diagram of the stent in FIG. 3.
Figure 8:
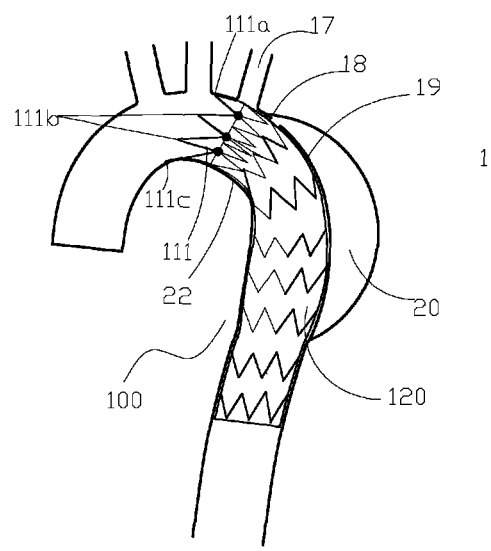
FIG. 8 is a schematic diagram of the stent in FIG. 3 after being implanted into the thoracic aorta.

According to FIG. 4 and FIG. 5, the bare wave-shaped ring 111 includes a plurality of greater curvature side proximal vertices 111a, a plurality of intermediate proximal vertices 111b, a plurality of lesser curvature side proximal vertices 111c, a plurality of corresponding distal vertices 111d, and supports 111e connecting the adjacent proximal vertex and the distal vertex. When the stent is implanted into the thoracic aorta, as shown in FIG. 8, the plurality of greater curvature side proximal vertices 111a are located in the vicinity of a greater curvature side 19 of an aorta 1, the plurality of lesser curvature side proximal vertices 111c are located in the vicinity of a lesser curvature side 22 of the aorta 1, and two parts of the intermediate proximal vertices 111b are respectively located between the greater curvature side proximal vertices 111a and the lesser curvature side proximal vertices 111c. There are two proximal vertices as shown in figures, but the number of the proximal vertices may be selected to be any other number according to the size or design of the stent. The distal vertices 111d correspond to the proximal vertices, the two may have the same number of vertices, and preferably the distal vertices 111d are all located in the same plane perpendicular to a longitudinal axis.

Figure 6:
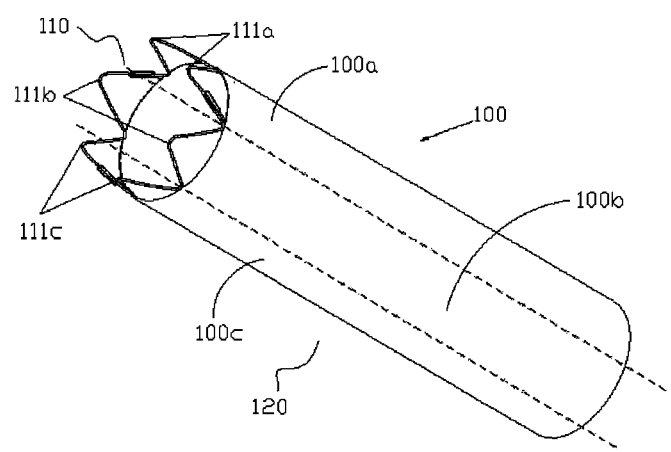
FIG. 6 is a partition schematic diagram of the stent in FIG. 2 along a peripheral direction.

Based on above, with reference to FIG. 6, the covered stent segment 120 of the stent 100 may be divided into a lesser curvature side region 100c and an opposite greater curvature side region 100a, and two opposite intermediate regions 100b located between the lesser curvature side region 100c and the greater curvature side region 100a along the peripheral direction, according to the implantation situation of the stent 100 in the thoracic aorta. In other words, of the covered stent segment 120, the lesser curvature side region 100c is an axial region containing the lesser curvature side proximal vertices 111c, the greater curvature side region 100a is an axial region containing the greater curvature side proximal vertices 111a, and the intermediate regions 100b are axial regions containing the intermediate proximal vertices 111b.

With reference to FIG. 3 and FIG. 4, the connecting assembly for rigidly connecting the bare stent segment 110 and the covered stent segment 120, includes a first connecting member 131, a first side connecting member 132 and a second side connecting member 133; the first connecting member 131 is arranged in the lesser curvature side region, and the first side connecting member 132 and the second side connecting member 133 are arranged in the two intermediate regions. The first side connecting member 132 and the second side connecting member 133 may be arranged in the same intermediate region, or respectively arranged in the two intermediate regions. Preferably, the first side connecting member 132 and the second side connecting member 133 are respectively arranged in the two intermediate regions, and symmetrically arranged with respect to the first connecting member 131. The connecting members are rigid metal sheets or metal struts made of nickel-titanium alloy. The first connecting member 131 is used for connecting the lesser curvature side support 111e between the lesser curvature side proximal vertex 111c and the distal vertex 111d, and the first proximal wave-shaped ring 121, connecting points on the first proximal wave-shaped ring 121 are located on support 121c between the distal vertex 121b and the proximal vertex 121a corresponding to the lesser curvature side support 111e. The "corresponding" mentioned here means that the distance between the support 111e and the corresponding support is the shortest compared to other supports of the first proximal wave-shaped ring 121.

Correspondingly, the first side connecting member 132 is used for connecting the support between the intermediate proximal vertex 111b and the distal vertex 111d on one side, and the support corresponding thereto on the first proximal wave-shaped ring 121; the second side connecting member 133 is used for connecting the support between the intermediate proximal vertex 111b and the distal vertex 111d on another side, and the support corresponding thereto on the first proximal wave-shaped ring 121.

The connecting assembly may be fixed with the bare wave-shaped ring 111 and the first wave-shaped ring 121 by the steel jacket or welding respectively. In the figure, the tail ends of the connecting members in the connecting assembly are respectively fixed with the bare wave-shaped ring 111 and the first wave-shaped ring 121 by using a second steel jacket 134, the specific implementation process is similar to that of the first steel jacket 124.

The bare stent segment 110 and the covered stent segment 120 are connected together by suturing, with reference to FIG. 3 to FIG. 5, the covered stent segment 120 further includes a wave-shaped ring 123 located between the bare wave-shaped ring 111 and the first wave-shaped ring 121, the wire diameter thereof is slightly smaller than that of other wave-shaped rings of the covered stent segment 120. For example, when the wire diameter of other wave-shaped rings is 0.55 mm, the wire diameter of the wave-shaped ring 123 may be 0.3 to 0.5 mm. And, compared with the other wave-shaped rings of the covered stent segment 120, the wave-shaped ring 123 includes more waveforms and less wave height, hence it is referred to as a small wave-shaped ring hereafter. For example, as the bare wave-shaped ring 111 with 6 waveforms, the small wave-shaped ring 123 has 12 waveforms.

Specifically as shown in FIG. 5, the small wave-shaped ring 123 includes a plurality of proximal vertices 123a, a plurality of distal vertices 123b, and supports 123c for connecting the adjacent proximal vertex 123a and distal vertex 123d. When the distal vertex 111d of the bare wave-shaped ring 111 is opposite to the proximal vertex 123a of the small wave-shaped ring 123, the two may be connected together by suturing with PTFE (Polytetrafluoroethylene) wire 127. Flexible connection is achieved by using PTFE wire, so that the overall flexibility of the stent may be ensured while the bare stent segment 110 is well apposed to the vessel wall.

Figure 7:
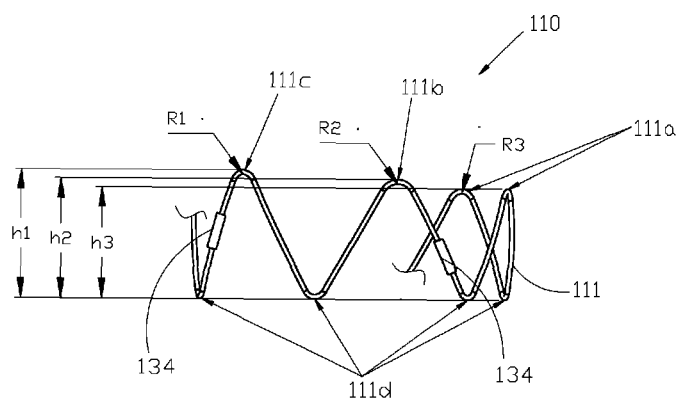
FIG. 7 is a schematic diagram of a preferred implementation method for a bare stent segment of the stent in FIG. 2.

With reference to FIG. 7, preferably, oriented from the lesser curvature side proximal vertices 111c to the greater curvature side proximal vertices 111a (i.e., the direction from the lesser curvature side region to the greater curvature side region), the wave heights of the bare wave-shaped ring 111 are gradually decreased, and the wave-shaped fillets thereof are gradually increased. The wave height mentioned here refers to a relative distance between the adjacent proximal vertex and the distal vertex; the wave-shaped fillet refers to a radius of curvature of a bending region near the proximal vertices or the distal vertices.

Specifically, the wave height h1 between the lesser curvature side proximal vertex 111c and the distal apex 111d is greater than that the height h2 between the intermediate proximal vertex and the distal vertex 111d, the height h2 is greater than that the height h3 between the greater curvature side proximal vertex 111a and the distal vertex 111d, and at this moment, the distal vertices 111d are all located in the same plane perpendicular to the longitudinal axis. Correspondingly, the wave-shaped fillet R1 of the lesser curvature side proximal vertex 111c is smaller than the fillet R2 of the intermediate vertex, and the fillet R2 is smaller than that the fillet R3 of the greater curvature side proximal vertex 111a.

As shown in FIG. 8, after the stent 100 is implanted into the thoracic aorta, the bare stent segment 110 is located near the left subclavian artery 17, and so it does not block the blood flowing into the branch vessels: the covered stent segment 120 covers a dissection crevasse 18, to prevent the blood flow from flowing into a dissection cavity 20 and forms a lumen for the blood flow passing therethrough, thereby to isolate the dissection. At the same time, at a place near the lesser curvature side 22 with a relatively small radius of curvature. i.e., an incurved region formed after the stent 100 is implanted, the stent 100 has a connecting assembly rigidly connecting the bare stent segment 110 and the covered stent segment 120, and through the constraints thereof, the bare stent segment 110 may be effectively prevented from overturning towards the vessel wall during the release process, so that the proximal end of the covered stent segment 120 is securely apposed to the wall, thereby avoiding the "turnover" effect.

For the connecting assembly, the first side connecting member 132 and the second side connecting member 133 thereof which are located in the intermediate regions of the stent 100 may further enhance the radial supporting force of the bare stent segment 110. Compared with the prior art, that is to say, in order to obtain larger radial supporting force, it is required of a metal wire with a relatively large wire diameter to form a wave-shaped ring, the bare stent segment 110 in the embodiment may form the wave-shaped ring by using a metal wire with a relatively smaller wire diameter while ensuring to have the same radial supporting force. Taking the plurality of wave-shaped rings in the covered stent segment 120 and adopting a metal wire with a wire diameter of 0.55 mm as an example, the bare stent segment 110 may adopt a metal wire with a wire diameter of 0.4 to 0.55 mm. The benefit of this is that, the smaller the wire diameter is, the smaller the radial supporting force of the wave-shaped ring can be, and the lesser the damage to the vessel wall is.

In addition, the connecting assembly does not have a corresponding rigid connecting member in the greater curvature side region, in order to prevent the bare stent segment 110 from forming a force upwarping towards the vessel wall during bending of the bare stent segment 110 here, thereby reducing the damage to the blood vessels on the greater curvature side.

Moreover, the wave height of the bare wave-shaped ring 111 in the greater curvature side region is relatively small, so that the bare wave-shaped ring 111 may be prevented from extending into the branch vessel. Meanwhile, the waveform fillet thereof is relatively large; therefore, the bending portion is smooth and not sharp, which reduces the damage degree to the branch vessels.

Figure 9:
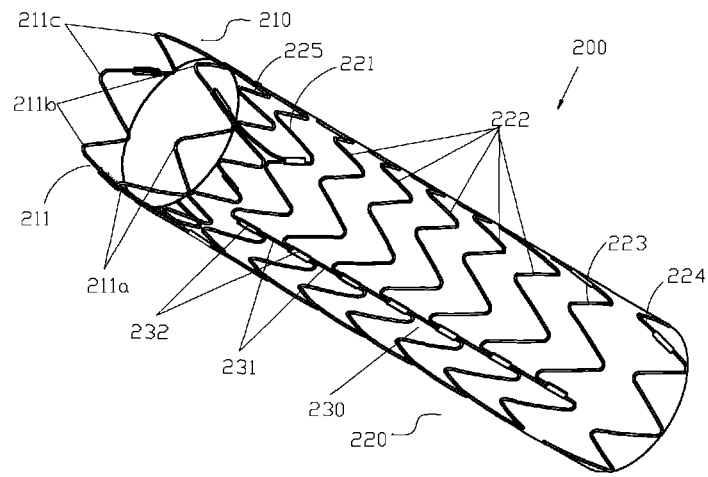
FIG. 9 is a schematic diagram of a thoracic aortic covered stent according to another embodiment of the present invention.
Figure 10:
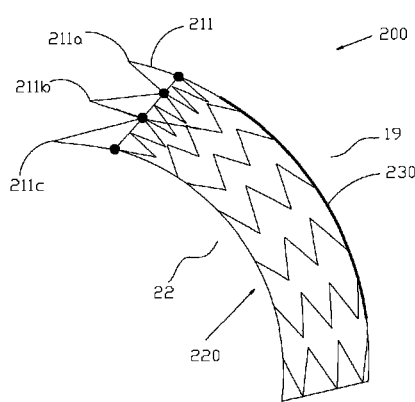
FIG. 10 is a diagram showing the stent in FIG. 9 having been implanted into the thoracic aorta.

With reference to FIG. 9 and FIG. 10, on the basis of the bracket 100 provided by the above embodiment, a stent 200 provided by another embodiment of the patent invention further includes a main body connecting assembly 230 for continuously and rigidly connecting a first proximal metal ring 221, a plurality of metal rings 222, and a second proximal metal ring 223 of the covered stent segment 220 in turn. The main body connecting assembly includes a plurality of third steel jackets 232, and a plurality of main body connecting members 231 connecting the adjacent steel jackets 232. The main body connecting member 231 is a rigid connecting strut or a connecting sheet, which may be made of nickel-titanium alloy. The main body connecting members 231 are connected to the first proximal metal ring 221, the plurality of metal rings 222 and the second proximal metal ring 223 through the third steel jackets 232, similar to the first and second steel jackets, the two ends of the metal wire are fixed together by the third steel jackets 232 to form a wave-shaped ring, meanwhile one end of the main body connecting members 231 is also fixed in one third steel jacket 232, in order to fix the main body connecting members 231 to the wave-shaped ring. Preferably, the third steel jackets 232 are located on the supports between the proximal vertices and the distal vertices of the wave-shaped ring.

Preferably, the main body connecting members 231 and the third steel jackets 232 are combined to form a linear main body connecting assembly 230. Moreover, the main body connecting assembly 230 is located in the greater curvature side region of the stent 200, and correspondingly the greater curvature side proximal vertices 211 of the bare stent segment 210 of the bare wave-shaped ring 211 are all located at the greater curvature side 19 after being implanted into the thoracic aorta. Similarly, the bare wave-shaped ring 211 further includes lesser curvature side proximal vertices 211c located at the lesser curvature side 22 after implantation, and two parts of intermediate proximal vertices 211b respectively located between the greater curvature side proximal vertices 211a and the lesser curvature side proximal vertices 211c.

The overall axial supporting performance of the covered stent segment 220 may be enhanced by setting the rigid linear main body connecting assembly 230 at the greater curvature side, thereby avoiding the covered stent segment 220 from being axially shortened. Moreover, the main body connecting assembly 230 connects to and terminates at the second proximal metal ring 223, and a first distal metal ring 224 is in a suspended state relative to the main body connecting assembly 230. Therefore, not only during the release process of the stent, but also during the post-operative forward process, the resilience force effect to the vessel wall applied by the distal end of the stent and induced by the rigid main body connecting assembly 230 may be avoided, thereby preventing the distal end of the stent from providing pressure on the vessel wall, and lessening the damage to the aorta by the distal end of the covered stent.

Figure 11:
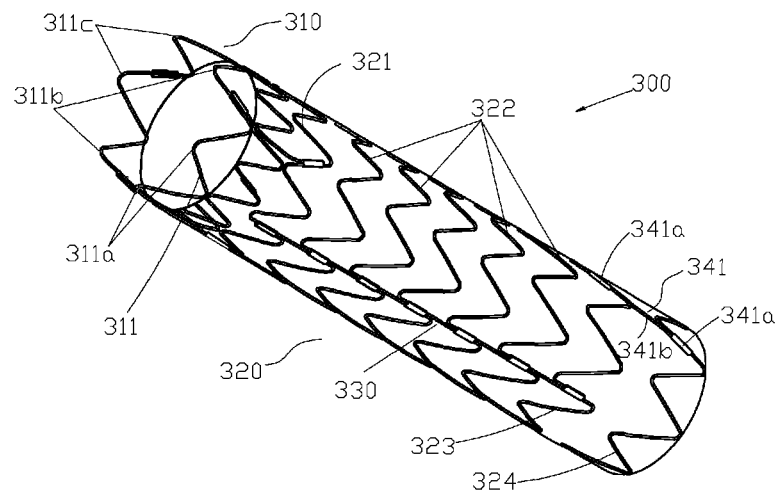
FIG. 11 is a schematic diagram of a thoracic aortic covered stent according to still another embodiment of the present invention.
Figure 12:
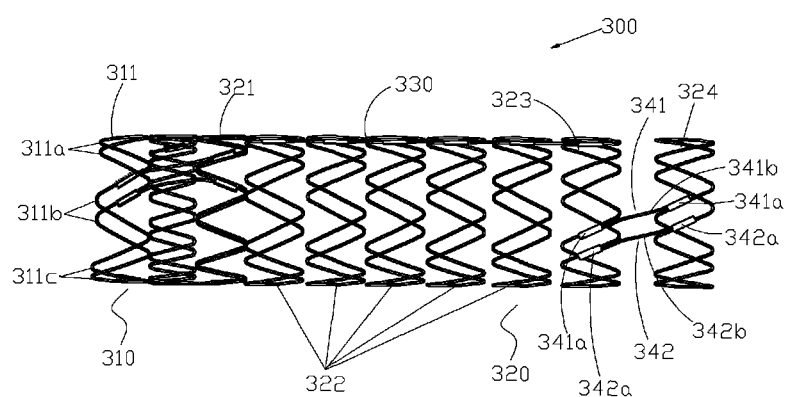
FIG. 12 is a schematic diagram of the stent in FIG. 11 from another view.
Figure 13:
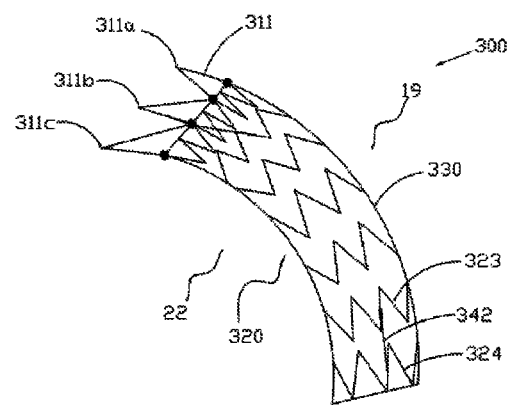
FIG. 13 is a diagram showing the stent in FIG. 11 having been implanted into the thoracic aorta.

With reference to FIG. 11 to FIG. 13, on the basis of the stent 200 provided on the above embodiment, a stent 300 provided by still another embodiment of the patent invention further includes distal connecting assemblies in the intermediate region of the stent for rigidly connecting a first distal metal ring 324 and a second distal metal ring 323, wherein there are two distal connecting assemblies: a first distal connecting assembly 341 and a second distal connecting assembly 342, which are symmetrically arranged with respect to the lesser curvature side region.

The first distal connecting assembly 341 includes two fourth steel jackets 341a respectively arranged on the first distal metal ring 324 and the second distal metal ring 323, and a first distal connecting member 341b connected between the two fourth steel jackets 341a. The first distal connecting member 341b is a rigid connecting strut or a connecting sheet, which may be made of nickel-titanium alloy. Similar to the first, second or third steel jackets, the two ends of the metal wire are fixed together by the fourth steel jackets 341a to form a wave-shaped ring, meanwhile one end of the first distal connecting member 341b is also fixed in the fourth steel jackets 341a, in order to fix the first distal connecting member 341b to the wave-shaped ring. Preferably, the fourth steel jackets 341a are located on the supports between the proximal vertices and the distal vertices of the wave-shaped ring. The structure of the second distal connecting assembly 342 is the same as that of the first distal connecting assembly 341, specifically not repeat them.

The first distal connecting assembly 341 and the second distal connecting assembly 342 are respectively arranged on two opposite sides of a main body connecting assembly 330, and corresponded to intermediate proximal vertices 311b of the bare wave-shaped ring 311 of the bare stent segment 310 (wherein two parts of the intermediate proximal vertexes 311b are respectively arranged between the greater curvature side proximal vertices 311a and the lesser curvature side proximal vertices 311c). After being implanted into the thoracic aortic vessels, the first distal connecting assembly 341 and the second distal connecting assembly 342 are respectively located in the intermediate regions between the greater curvature side 19 and the lesser curvature side 22 of the thoracic aorta, and arranged oppositely.

As stated above, the linear main body connecting assembly 330 is used for continuously connecting a first proximal wave-shaped ring 321, a plurality of wave-shaped rings 322 and a second distal wave-shaped ring 323 in sequence, there is no connection between the first distal metal ring 324 and the second distal metal ring 323 by the main body connecting assembly 330, so that the damage to the vessel wall caused by the resilience force of the distal end of the stent may be avoided. However, because the first distal metal ring 324 and the second distal metal ring 323 are only in flexible connection formed by the membranes, which lac rigid constraints, the two rings can be positioned closer during the release process of the stent and the post-operative forward process, the distal end of the stent may enter an aneurysm cavity during shortening to the proximal end, so that the aneurysm may not be fully covered by the covered stent segment, resulting in the generation of I type endoleak. In the present embodiment, the first distal connecting assembly 341 and the second distal connecting assembly 342 are additionally arranged between the first distal metal ring 324 and the second distal metal ring 323, to enhance the stability of the distal end to the stent and reduce the risk of the stent shortening towards the dissection or aneurysm body. Meanwhile, the distal connecting assembly is arranged in the intermediate regions between the greater curvature side region and the lesser curvature side region, and the damage to the vessel wall caused by the resilience force of the stent may be avoided.

Figure 14:
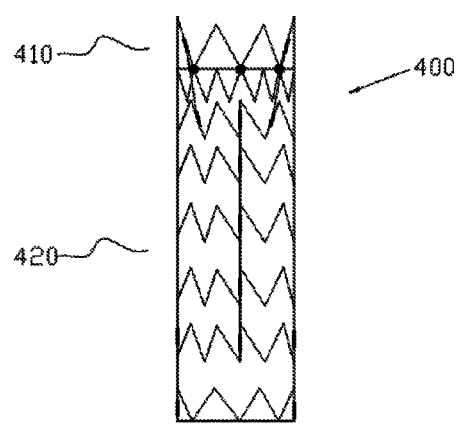
FIG. 14 is a schematic diagram of a straight tube-shaped stent provided by an embodiment of the present invention.
Figure 15:
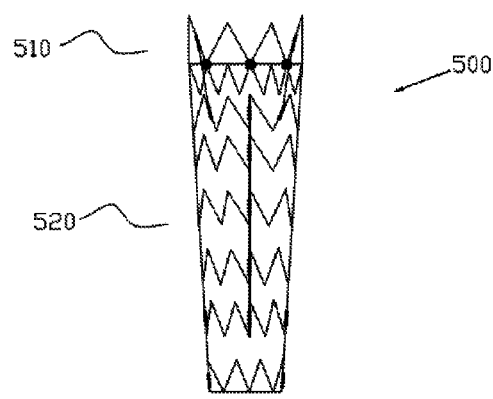
FIG. 15 is a schematic diagram of a truncated cone-shaped stent provided by an embodiment of the present invention.

It is worth mentioning that the stent according to the present invention may be straight tube-shaped or hollow truncated cone-shaped. With reference to FIG. 14, the straight tube-shaped stent 400 may be one of the stents 100, 200 and 300, and the diameter of a lumen formed by a bare stent segment 410 after the stent is released is equal to that of a lumen formed by a covered stent segment 420. With reference to FIG. 15, the truncated cone-shaped stent 500 may be one of the stents 100, 200 and 300, the radius length of a lumen formed by a covered stent segment 520 is the largest at the proximal end connected to a bare stent segment 510, the smallest at the distal end and gradually changed in the middle connected to.

The invention claimed is:

1. A thoracic aortic covered stent, comprising a bare stent segment and a covered stent segment, the bare stent segment comprising a bare wave-shaped ring; the covered stent segment having a lesser curvature side region, a greater curvature side region, and two opposite intermediate regions respectively located between the lesser curvature side region and the greater curvature side region; and the covered stent segment comprising a first proximal wave-shaped ring, wherein the thoracic aortic covered stent further comprises exactly three connecting members: a first connecting member, a first side connecting member and a second side connecting member, all being connected to the bare wave-shaped ring and the first proximal wave-shaped ring; the first connecting member is arranged in the lesser curvature side region, and the first side connecting member and the second side connecting member are arranged in the two intermediate regions respectively;

wherein the covered stent segment further comprises a plurality of wave-shaped rings, a second distal wave-shaped ring and a first distal wave-shaped ring arranged from the proximal end to the distal end: the stent further comprises a linear main body connecting assembly in the greater curvature side region for rigidly connecting the first proximal wave-shaped ring, the plurality of wave-shaped rings and the second distal wave-shaped ring in sequence; and wherein the stent further comprises a distal connecting assembly in the intermediate regions for rigidly connecting the first distal wave-shaped ring and the second distal wave-shaped ring.

2. The thoracic aortic covered stent according to claim 1, characterized in that the bare wave-shaped ring and the first proximal wave-shaped ring both comprise wave peaks, wave troughs and supports connected and arranged between the wave peaks and the wave troughs, and wherein two ends of the first connecting member, the first side connecting member and the second side connecting member are both connected to the supports respectively.

3. The thoracic aortic covered stent according to claim 2, characterized in that the first connecting member, the first side connecting member and the second side connecting member are all connected to the supports through steel jackets.

4. The thoracic aortic covered stent according to claim 1, characterized in that the main body connecting assembly comprises a plurality of connecting members for rigidly connecting the adjacent wave-shaped rings.

5. The thoracic aortic covered stent according to claim 1, characterized in that, as oriented from the lesser curvature side region to the greater curvature side region, the wave height of the bare wave-shaped ring is gradually decreased, and the waveform fillet thereof is gradually increased.

6. The thoracic aortic covered stent according to claim 1, characterized in that there are two distal connecting assemblies symmetrically arranged with respect to the lesser curvature side region.

7. The thoracic aortic covered stent according to claim 1, characterized in that the first connecting member is the only connecting member in the lesser curvature side region.

8. A thoracic aortic covered stent, comprising a bare stent segment and a covered stent segment, the bare stent segment comprising a bare wave-shaped ring; the covered stent segment having a lesser curvature side region, a greater curvature side region, and two opposite intermediate regions respectively located between the lesser curvature side region and the greater curvature side region; and the covered stent segment comprising a first proximal wave-shaped ring, wherein the thoracic aortic covered stent further comprises a first connecting member, a first side connecting member and a second side connecting member, all being connected to the bare wave-shaped ring and the first proximal wave-shaped ring; the first connecting member is arranged in the lesser curvature side region, and the first side connecting member and the second side connecting member are arranged in the two intermediate regions respectively;

wherein the covered stent segment further comprises a plurality of wave-shaped rings, a second distal wave-shaped ring and a first distal wave-shaped ring arranged from the proximal end to the distal end; the stent further comprises a main body connecting assembly in the greater curvature side region for rigidly connecting the first proximal wave-shaped ring, the plurality of wave-shaped rings and the second distal wave-shaped ring in sequence; and wherein the stent further comprises a distal connecting assembly in the intermediate regions for rigidly connecting the first distal wave-shaped ring and the second distal wave-shaped ring.

9. The thoracic aortic covered stent according to claim 8, characterized in that there are two distal connecting assemblies symmetrically arranged with respect to the lesser curvature side region.

10. A thoracic aortic covered stent, comprising a bare stent segment and a covered stent segment, the bare stent segment comprising a bare wave-shaped ring; the covered stent segment having a lesser curvature side region, a greater curvature side region, and two opposite intermediate regions respectively located between the lesser curvature side region and the greater curvature side region; and the covered stent segment comprising a first proximal wave-shaped ring, wherein the thoracic aortic covered stent further comprises a first connecting member, a first side connecting member and a second side connecting member, all being connected to the bare wave-shaped ring and the first proximal wave-shaped ring: the first connecting member is arranged in the lesser curvature side region, and the first side connecting member and the second side connecting member are arranged in the two intermediate regions respectively, and wherein the covered stent further comprises a wave-shaped ring located between the bare wave-shaped ring and the first proximal wave-shaped ring, the bare wave-shaped ring and the said wave-shaped ring being connected by suturing.

* * * * *